United States Patent [19]

Moser, Jr. et al.

[11] 4,065,516

[45] Dec. 27, 1977

[54] COMBINATION ISOMERIZATION-ALKYLATION PROCESS

[75] Inventors: John F. Moser, Jr.; William C. Behrmann, both of Baton Rouge, La.

[73] Assignee: Exxon Research and Engineering Company, Linden, N.J.

[21] Appl. No.: 642,538

[22] Filed: Dec. 19, 1975

[51] Int. Cl.² .............................................. C07C 3/54
[52] U.S. Cl. .............................................. 260/683.47
[58] Field of Search ..................... 260/683.43, 683.58, 260/683.47, 683.2

[56] References Cited

U.S. PATENT DOCUMENTS

| | | | |
|---|---|---|---|
| 2,429,205 | 10/1947 | Jenny et al. | 260/683.43 |
| 2,591,367 | 1/1952 | McAllister | 260/683.47 |
| 3,592,868 | 7/1971 | Heckelsberg | 260/683.2 |
| 3,763,261 | 10/1973 | Sobel | 260/683.43 |
| 3,766,293 | 10/1973 | Parker et al. | 260/683.58 |
| 3,887,635 | 6/1975 | Parker et al. | 260/683.58 |

Primary Examiner—George Crasanakis
Attorney, Agent, or Firm—John W. Ditsler

[57] ABSTRACT

Alkylates of enhanced product quality are prepared by isomerizing a mixed butenes-containing feed prior to alkylating said feed with a saturated hydrocarbon, preferably an isoparaffin, in the presence of a catalyst comprising a strong acid such as halosulfuric acid, trihalomethanesulfonic acid or mixtures thereof and a moderator containing at least one oxygen atom per molecule. A preferred catalyst is fluorosulfuric acid and water.

8 Claims, No Drawings

COMBINATION ISOMERIZATION-ALKYLATION PROCESS

BACKGROUND OF THE INVENTION

1. Field of the Invention

The present invention is concerned with a combination isomerization/alkylation process. More particularly, the invention relates to isomerizing a mixed butenes-containing feed such that at least a portion of the butene-1 is converted to butene-2 prior to alkylating an isoparaffinic hydrocarbon with at least a portion of the isomerized feed to produce more highly branched hydrocarbons.

2. Description of the Prior Art

The use of catalytic alkylation processes to produce branched chain hydrocarbons having valuable antiknock properties that are suitable for use as gasoline blending components is well known in the petroluem refining art. Generally, the alkylation of saturated hydrocarbons, such as isoparaffins, with olefins is accomplished by contacting the reactants with an acid catalyst, such as sulfuric acid, fluorosulfuric acid or a halogen acid, such as hydrofluoric acid, to form a reaction mixture, settling said mixture to separate the catalyst from the hydrocarbons, and further separating the hydrocarbons, for example by fractionation, to recover the alkylation reaction product. The alkylation reaction product is normally a mixture of $C_5$-$C_{10}$ paraffins, often termed "alkylate", and typically contains a mixture of $C_8$-$C_9$ hydrocarbons, the composition of which depends upon the particular isoparaffinic and olefinic reactants utilized. The formation of more highly branched hydrocarbons, e.g., trimethylpentanes, rather than less branched hydrocarbons, e.g., dimethylhexanes, is preferred because the former provide a higher octane gasoline blending stock.

The formation of an alkylate of improved quality by isomerizing a mixed butenes-containing feed (one containing butene-1, butene-2, and isobutene), i.e. shifting the double bond in the organic molecule from a terminal position to a more central position such as occurs when forming butene-2 from butene-1, prior to alkylating a paraffin, particularly an isoparaffin, with the resulting isomerate has also been suggested for several alkylation catalysts, particularly sulfuric acid and hydrofluoric acid (see, for example, U.S. Pat. Nos. 2,377,352; 2,429,205; 2,450,039; 2,460,303; 2,502,015; 2,591,367; 2,594,393; 3,763,261, and 3,800,003). As an example, Example II of U.S. Pat. No. 2,591,367 contains the following data for alkylation in the presence of 96% sulfuric acid:

|  | Untreated Feed | Isomerized Feed |
| --- | --- | --- |
| Composition of Feed |  |  |
| Propane-propylene | 0.4 | — |
| Isobutene | 5.1 | 0.1 |
| Butene-1 | 4.4 | 1.5 |
| Butene-2 | 4.9 | 10.2 |
| Isobutane | 71.5 | 53.4 |
| Normal butane | 13.7 | 34.8 |
| Quality of Product |  |  |
| Octane No. of Alkylate | 92.5 | 93.7 |

However, as will be discussed hereinbelow, the substantial removal of isobutene, which produces a relatively low octane alkylate, i.e. 85–90 unleaded motor octane number (MONC), from the isomerized feed could well have produced a large portion of the increased octane number rather than the isomerization of butene-1 to butene-2.

In the case of hydrofluoric acid, Examples I and II in U.S. Pat. No. 2,502,015 indicate that the alkylate produced from reacting isobutane and butene-1 without a preliminary isomerization step has an ASTM octane number of about 88.9. This compares with an octane number of about 92.5 obtained when the butene-1 present in the effluent from the isomerization step is removed therefrom prior to alkylation. In addition, the data in Examples IV and V indicate that alkylation with butene-2 rather than butene-1 provides an octane number advantage of 3.5 and 3.8, respectively. Thus, the teachings of the U.S. Pat. No. 2,502,015 indicate that the difference in alkylate quality between butene-1 and butene-2 ranges from about 3.5 to about 3.8 octane. Similarly, if the octane number and feed composition data in U.S. Pat. No. 2,594,343 is extrapolated to the pure isomers, the octane numbers obtained for butene-1 and butene-2 are 92.6 and 95.8, respectively, a difference of 3.2.

A similar result may be obtained by comparing Runs 2 and 5 of Table 1 in U.S. Pat. No. 3,800,003. As separate feedstocks, butene-1 and isobutene provided alkylates which when blended together in equal amounts gave 94.1 MONC. As separate feedstocks, butene-2 and isobutene gave alkylates which when blended together in equal amounts gave 96.2 MONC. Assuming the contribution from isobutene was the same in each case, the alkylate formed from butene-2 was about 4.2 MONC better than that from butene-1.

The above data indicate that the alkylate produced using butene-2 is from 3–4 MONC superior to that obtained with butene-1 for hydrofluoric acid alkylation. Thus, it would be expected that converting butene-1 to butene-2 prior to hydrofluoric acid alkylation would produce an improved alkylate.

However, it has been found that for the alkylation process described in U.S. Pat. No. 3,887,635, the disclosures of which are incorporated herein by reference, isomerization of a mixed butenes-containing feed prior to alkylation provides an improved alkylate even though alkylation of butene-1 or butene-2 in said process produces an alkylate of substantially equivalent octane number.

SUMMARY OF THE INVENTION

Now according to the present invention, it has been found that an alkylate of improved quality is produced from a paraffin and a mixed butenes-containing feed according to a combination process which comprises (1) contacting said feed with an isomerization catalyst in an isomerization zone at olefin isomerization conditions to form an isomerate enriched in butene-2 and (2) contacting at least a portion of said isomerate with said paraffin in the presence of an alkylation catalyst in an alkylation zone at alkylation conditions. The alkylation catalyst employed herein is formed from (1) a halosulfuric acid of the formula $XSO_3H$, trihalomethanesulfonic acid of the formula $CX_3SO_3H$, X being a halogen, or mixtures thereof and (2) one or more moderators containing at least one oxygen atom per molecule. This result is totally unexpected in view of the prior art since it has also been found that butene-1 or butene-2, when alkylated with the catalyst described above, produces a substantially equivalent alkylate. This surprising result is believed due to an antagonism between butene-1 and isobutene that would occur were the butene-1 not converted to butene-2 during isomerization. A preferred alkylation catalyst is fluorosulfuric acid and water.

DETAILED DESCRIPTION OF THE INVENTION

The mixed butenes-containing feed to the isomerization process of the present invention may comprise solely butene isomers or may contain other olefinic reactants as well as hydrocarbons including, for example, paraffins and naphthenes. Minor amounts of contaminants such as diolefins, acetylenes, mercaptans, aliphatic sulfur, water, caustic and the like may also be present. Such contaminants should be minimized, i.e. be less than about 1 wt. % although larger amounts may be present, since each will cause increased acid consumption during subsequent alkylation. In addition to the mixed butenes, other olefinic reactants that may be present include $C_2$-$C_{12}$ terminal and internal monoolefins such as ethylene, propylene, the isomeric pentenes and similar higher monoolefinic hydrocarbons of either a straight chain or a branched chain structure. Preferably, the $C_2$-$C_6$ monoolefins are used, although the highly branched $C_7$-$C_{12}$ monoolefins may also be used. Cycloolefins may also be used. Although it is desirable from an economic standpoint to use the normally gaseous olefins as reactants, normally liquid olefins may be used. Thus, the invention contemplates the use of reactable polymers, copolymers, interpolymers, crosspolymers, and the like, of the abovementioned olefins, such as, for example, the diisobutylene and the triisobutylene polymers, the codimer of normal butylene and isobutylene, of butadiene and isobutylene, and the like. Mixtures of two or more of the olefins above described can be used as the process feedstock.

Suitable paraffinic hydrocarbon feedstocks for use in the present invention comprise straight and/or branched chain $C_2$-$C_{10}$ paraffins such as hexane, butane and the like, and preferably $C_4$-$C_6$ isoparaffins such as isobutane, isopentane, isohexane, and the like. While open chain hydrocarbons are preferred, cycloparaffins such as cyclopropane may also be used. The alkylation step of the present invention also contemplates the use of various refinery cuts as feedstocks. Thus, $C_2$, $C_3$, $C_4$ and/or $C_5$ olefin cuts from thermal and/or catalytic cracking units; field butanes which have been subjected to prior isomerization and partial dehydrogenation treatment; refinery stabilizer bottoms; spent gases; normally liquid products from sulfuric acid or phosphoric acid catalyzed polymerization and copolymerization processes; and products, normally liquid in character, from thermal and/or catalytic cracking units, are all excellent feedstocks for the present alkylation process. Such feeds are preferably dried, i.e. about 5 to 15 wppm of water, before entering the reactor to control excess water buildup.

In the process of the present invention, the mixed butenes-containing feed is first contacted with an isomerization catalyst in an isomerization zone at olefin isomerization conditions. Isomerization catalysts which can be suitably employed include catalysts which produce a shift of the olefinic bond in butene-1 to a more central position in the hydrocarbon molecule to form butene-2. Various catalysts have been found suitable in prior art and include, for example, alumina, silica, zirconia, chromium oxide, boron oxide, thoria, magnesia, aluminum sulfate, and combinations of two or more of the foregoing. Also employed have been acidic catalysts such as sulfuric acid, phosphoric acid, aluminum chloride, etc., either in solution or on a solid support. Also suitable for use as an isomerization catalyst is a boron halide-modified metal oxide such as boron halide-modified substantially anhydrous or hydrous alumina. In addition, hydrogenation-dehydrogenation type catalysts such as nickel or palladium on alumina or palladium on an inert support may be satisfactorily employed as isomerization catalysts. Thermal isomerization may be utilized, but suffers from the defect of producing excessive amounts of side products.

The particular isomerization process employed is not critical to the practice of the present invention. It may be conducted in either batch or in a continuous operation, such as described in U.S. Pat. No. 3,800,003, the disclosure of which is incorporated herein by reference, although a continuous operation is preferred. Since the isomerization process employed in the present invention is well known in the art, only typical isomerization conditions are summarized below:

|  | Suitable | Preferred |
|---|---|---|
| Temperature, ° F | 0–800 | 100–300 |
| Pressure, atm. | 1–200 | 10–100 |
| Space Velocity, v/h/v | 0.1–40 | 0.1–20 |

The isomerization process can be suitably conducted in the gas phase although liquid phase operation is preferred. The process should be operated in a manner to maximize the conversion of butene-1 to butene-2. Thus, at least 50, preferably at least 70, and most preferably at least 90% of the butene-1 will be isomerized to butene-2. This will favor the production of an alkylate of improved quality since, as described hereinafter, it is believed there is an antagonism between butene-1 and isobutene when the two isomers contact each other in the presence of the catalyst system described hereinbelow.

While not wishing to be bound by any particular theory, it is postulated that when a feed containing butene-1, butene-2 and isobutene is contacted with the present alkylation catalyst, the isobutene is protonated and forms t-butyl carbonium ion according to the following reaction:

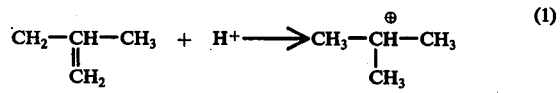

(1)

This causes the concentration of t-butyl carbonium ion in the vicinity of the acid phase/hydrocarbon phase interface within the alkylation zone to increase which results in an increased tendency for any butene-1 present to react with the t-butyl carbonium ion and be alkylated to dimethylhexane, a component having a relatively low octane, i.e. between about 65–70 MONC. The increased formation of the dimethylhexanes as described above results in the production of a lower octane alkylate. This effect is not observed with butene-2 which reacts with the t-butyl carbonium ion to form trimethylpentanes, a high octane component having an average MONC of about 99.6. Thus, prior to alkylating a paraffin with a feed containing butene-1, butene-2 and isobutene, at least a portion, preferably a substantial portion, of the butene-1 should be converted to butene-2 to increase the selectivity to trimethylpentanes rather than to lower octane components such as dimethylhexanes.

The isomerate thus produced is then contacted with a paraffin to provide an alkylate superior to that produced by conventional alkylation processes. It is preferred that the paraffin be substantially free of butene-1.

The alkylation process used in the present invention is that described in U.S. Pat. No. 3,887,635 which relates to the alkylation of a saturated hydrocarbon with an olefin in the presence of a catalyst mixture formed from a strong acid such as a halosulfuric acid of the formula $XSO_3H$, trihalomethanesulfonic acid of the formula $CX_3SO_3H$, X being a halogen, or mixtures thereof and one or more moderators, generally containing at least one oxygen atom per molecule and including water, aliphatic and cycloaliphatic alcohols and ethers, aliphatic, cycloaliphatic and aromatic sulfonic and carboxylic acids and their derivatives and inorganic acids. The term "moderator" as used herein, is defined as a compound which, in combination with a strong acid, produces a catalyst system of increased selectivity, resulting in an alkylate of enhanced product quality.

The catalyst moderators may be used effectively with a wide variety of strong acids. Examples of strong acid components of the strong acid-moderator catalyst system include halosulfuric acid such as fluorosulfuric acid, chlorosulfuric acid and bromosulfuric acid; trihalomethanesulfonic acid such as trifluoromethanesulfonic acid, trichloromethanesulfonic acid and tribromomethanesulfonic acid; or mixtures thereof and the like. Preferred strong acids include fluorosulfuric acid, trifluoromethanesulfonic acid or mixtures thereof. In addition, the phosphorus analog of trihalomethanesulfonic acid, i.e. trihalomethanephosphonic acid, may be an effective strong acid.

The amount of moderator used in forming the catalyst system is an important variable in the production of high quality alkylate, the appropriate amount varying depending, in part, upon the alkylation temperature. Thus, for example, at temperatures between about, say, 0° and 40° F, useful amounts of moderator can range between about 5 and 45 mole % based on acid (moles of moderator per 100 moles) of acid), preferably between 10 and 30 mole % and still more preferably between 15 and 25 mole %, e.g., 20 mole %. In some instances, however, it may be desirable to use somewhat lower or higher amounts of moderator, e.g., 50 mole % based on acid, where, for example, increased catalyst selectivity is desired.

At higher alkylation temperatures, say, between about 40° and 100° F, increased amounts of moderator may be desirable due to the increased strong acid activity. Thus, an amount of moderator ranging between about 50 and 100 mole % based on acid at these higher temperatures may be employed. In fact, under appropriate conditions, these higher amounts of moderator may also be utilized at the lower temperatures disclosed hereinabove, if desired.

In the case of hydroxyl-containing moderators (or moderators containing hydroxyl precursors, i.e. latent hydroxyl groups), amounts of moderator added to the strong acid may fall below the above-specified ranges. It appears that the efficiency of hydroxy compounds is directly related to the overall number of hydroxyl groups or latent hydroxyl groups present per molecule. Thus, ethanol with one hydroxyl group should have moderator activity similar to 0.5 mole of ethylene glycol with two hydroxyl groups. Hence, as the number of hydroxyl groups or latent hydroxyl groups per molecule of moderator increases, the required amount of moderator compound will decrease.

Although the broad concentration ranges are generally independent of the type of moderator used, the preferred or optimal range will vary depending on the structure of the moderator, the reaction temperature, the concentration and nature of the olefin in the feed and the olefin space velocity.

Typical operating conditions for the alkylation process described in U.S. Pat. No. 3,887,635 are summarized below:

|  | Suitable | Preferred |
|---|---|---|
| Temperature, ° F | −80 to +100 | −20 to +40 |
| Total Pressure, atm. | 1 to 20 | 1 to 10 |
| Olefin Space Velocity, v/h/v | 0.05 to 1000 | 0.05 to 1.0 |
| Contact time, min | 0.002 to 60+ | 5 to 45 |
| Paraffin/Olefin Vol. Ratio in external feed | 2:1 to 200:1 | 5:1 to 20:1 |
| Paraffin/Olefin Vol. Ratio in reaction zone | 10:1 to 20,000:1 | 20:1 to 2,000:1 |

In general, it is preferable to maintain the reactants substantially in the liquid phase although a vapor phase operation is also contemplated. Autorefrigerated reactors and the like may be employed to maintain liquid phase operation. Where the reaction is carried out at temperatures above about 10° F, it is necessary that the reaction be conducted under superatmospheric pressure, if both the reactants and catalyst are to be maintained substantially in the liquid state. The volume % of total catalyst in the reaction mixture or emulsion (when liquid phase operations are used) in the reactor can range from about 30 to 80 volume % based on total reaction mixture and preferably from about 50 to 70 volume %. The isoparaffin concentration, including alkylate, in the hydrocarbon phase, (in a liquid phase process), can range from 40 to 100 volume % based on the total volume of the hydrocarbon phase and preferably from 50 to 90 volume %. Such isoparaffin concentrations can be maintained by recycling unreacted isoparaffin to the reactor.

The process may be carried out either as a batch or continuous type of operation, although it is preferred for economic reasons to carry out the process continuously. It has been generally established that in alkylation processes, the more intimate the contact between the feedstock and the catalyst the better the yield of saturated product obtained. With this in mind, the present process, when operated as a batch operation, is characterized by the use of vigorous mechanical stirring or shaking of the reactants and catalyst.

In continuous operations, in one embodiment, reactants may be maintained at sufficient pressures and temperatures to maintain them substantially in the liquid phase and then continuously forced through dispersion devices into the reaction zone. The dispersion devices may be jets, porous thimbles and the like. The reactants are subsequently mixed with the catalyst by conventional mixing means such as mechanical agitators and the like. After a sufficient time, the product can then be continuously separated from the catalyst and withdrawn from the reaction system while the partially spent catalyst is recycled to the reactor. If desired, a portion of the catalyst can be continuously regenerated or reactivated by any suitable treatment and returned to the alkylation reactor.

In another embodiment of the invention, the catalyst employed may be incorporated with a suitable solid carrier or support. Any solid carrier may be used that is substantially inert to the catalyst under the reaction conditions. Active supports may be rendered inert by coating them with an inert material such as antimony trifluoride or aluminum trifluoride. Examples of such carriers include silica gel, anhydrous $AlF_3$, aluminum phosphate, carbon, coke, firebrick and the like. When supported catalysts are used, the reactants, in vapor and/or liquid form, are contacted with the catalyst particles at conversion conditions. The catalyst materials may be maintained in a fixed bed, moving bed or fluid bed reaction zone.

As in other alkylation processes, more accurate control of the quality of the final product may be obtained if the reaction system is provided with a recycling feature wherein the partially converted hydrocarbons are mixed with fresh feed and returned to the feed dispersion device in the reactor. However, due to the high conversion efficiency of the present catalyst system, it is preferred to effect alkylation in a once-through operation with short reaction times.

In general, reaction and/or recovery schemes and apparatus employed in conjunction with prior art liquid acid catalyst systems can be used with the catalyst systems of the present invention. Examples of potentially applicable process techniques and apparatus are described in U.S. Pat. Nos. 2,433,944; 2,479,366; 2,701,184; 2,717,913; 2,775,636, U.K. Pat. Nos. 543,046; 577,869; 731,806; 738,348; 803,458; 804,966 and 881,892, the disclosures of which are incorporated herein by reference.

While the present invention has been described with regard to forming an enhanced alkylate by isomerizing mixed butenes so as to shift the double bond from a terminal to a more central position, it should be clearly understood that improved product quality can be obtained by isomerizing a feed containing pentene-1 and pentene-2. In particular, shifting the double bond in the linear pentenes from a central position to a more external position, i.e. isomerizing pentene-2 to pentene-1, will favor the formation of an alkylate having enhanced product quality because pentene-1 forms a higher octane component than pentene-2. Very little alkylate enhancement was observed for isomerizing the branched pentene isomers since they give about the same octane alkylate.

The present invention may be better understood by reference to the following examples which are presented for illustrative purposes only and are not intended to unduly restrict the limits of the claims appended hereto.

EXAMPLE 1

Fluorosulfuric acid alkylation with pure butenes 189 cc of a catalyst comprising fluorosulfuric acid, water, and an organic promoter was introduced by vacuum into a 315 cc stainless steel loop reactor immersed in a constnt temperature bath. The organic promoter referred to herein is formed naturally during an alkylation reaction. However, in the present examples, it was obtained from spent alkylation catalyst and then added to the reactor to simulate an equilibrium catalyst mixture (see Miron, S., and Lee, R.J., J. Chem. Eng. Data, Vol. 8, No. 1, p. 150-160, 1963 for a more detailed description of the organic promoter). Isobutane was then charged to the reactor until the reactor was full of the hydrocarbon/catalyst mixture and the total pressure was between about 75-125 psig. The catalyst represented about 60 volume % of the reactor charge. The initial fill of isobutane served to minimize degradation reactions when the olefin was introduced. The catalystisobutane mixture was then emulsified and circulated by a pump and allowed to equilibrate thermally. A hydrocarbon feedstock was introduced into the circulating emulsion and the hydrocarbon phase allowed to equilibrate. This required of about 2 hours. The product was withdrawn from the reactor into a settler wherein the hydrocarbon was separated from the acid. The acid was returned to the reactor. A sample of the hydrocarbon was then analyzed by gas chromotography and the octane calculated from the compositions obtained therefrom. The results from the experiment are shown in Table 1 below:

Table 1

| Feed Olefin | Isobutene | Butene-1 | Butene-2 |
|---|---|---|---|
| Catalyst | | | |
| Water/Acid mole ratio | | —0.35— | |
| Organic Promoter, wt.% on total catalyst | | —8— | |
| Feed Composition, Vol. % | | | |
| Isobutane | 81.2 | 80.0 | 81.0 |
| n-butane | 10.1 | 10.6 | 10.0 |
| Olefin | 8.7 | 9.4 | 9.0 |
| Operating Conditions | | | |
| Temperature, °F | | —40— | |
| Olefin Space Velocity, v/h/v | 0.21 | 0.23 | 0.22 |
| Emulsion Circulation Rate, gpm | 23 | 22 | 26 |
| Product Selectivity, Vol. % on $C_6^+$ Alkylate | | | |
| $C_5$ | 4.8 | 0.6 | }0.98 |
| $C_6$ | 3.75 | 0.57 | |
| $C_7$ | 3.18 | 0.69 | — |
| Trimethylpentanes | 67.08 | 92.83 | 93.6 |
| Dimethylpentanes | 8.50 | 5.05 | 4.49 |
| Methylheptanes | 0.13 | — | — |
| $C_9^+$ | 17.37 | 0.85 | 0.93 |
| $C_6^+$ MONC | 92.7 | 97.4 | 97.6 |

This data shows that four fluorosulfuric acid alkylation using pure butene feedstocks, bentene-1 and butene-2 gave about the same alkylate quality while that obtained using isobutene was much lower.

EXAMPLE 2

Fluorosulfuric Acid and Sulfuric Acid Alkylation with Mixed Butenes

The procedure of Example 1 was followed using a fluorosulfuric acid and a sulfuric acid catalyst. The results from these experiments are shown in Table 2.

TABLE 2

| Acid | Fluorosulfuric | | | | | Sulfuric | | | |
|---|---|---|---|---|---|---|---|---|---|
| Run No. | 1 | 2 | 3 | 4 | 5 | 6 | 7 | 8 | 9 |
| Catalyst | | | | | | | | | |
| $H_2O$/Acid, Mole ratio | —0.35— | | | | | Equilibrium 95.8 Wt. % Titratable Acidity Catalyst from a Commercial Unit (2 wt. % $H_2O$ on total catalyst) | | | |

TABLE 2-continued

| Acid | Fluorosulfuric | | | | | Sulfuric | | | |
|---|---|---|---|---|---|---|---|---|---|
| Run No. | 1 | 2 | 3 | 4 | 5 | 6 | 7 | 8 | 9 |
| Organic Promoter, Wt. % on Total Catalyst | | | 8 | | | | | 3 | |
| Feed Composition, Vol. % | | | | | | | | | |
| Butene-1 | 1.9 | 0 | 3 | 1 | 0 | 1.9 | 0 | 1 | 0 |
| Butene-2 | 4.5 | 6.4 | 3 | 5 | 6 | 4.5 | 6.4 | 5 | 6 |
| Isobutene | 1.5 | 1.5 | 3 | 3 | 3 | 1.5 | 1.5 | 3 | 3 |
| Isobutane | 82.7 | 82.7 | 81 | 81 | 81 | 82.7 | 82.7 | 81 | 81 |
| n-butane | 9.4 | 9.4 | 10 | 10 | 10 | 9.4 | 9.4 | 10 | 10 |
| Operating Conditions | | | | | | | | | |
| Temperature, °F | 39 | 38 | 40 | 37 | 38 | 41 | 41 | 42 | 42 |
| Olefin Space Vel. v/h/v | 0.19 | 0.19 | 0.19 | 0.22 | 0.22 | 0.19 | 0.19 | 0.22 | 0.22 |
| Emulsion Circulation Rate, gpm | 24 | 25 | 27 | 27 | 31 | 21 | 21 | 52 | 51 |
| Product Distribution, Vol. % on $C_6^+$ Alkylate | | | | | | | | | |
| $C_6$ and $C_7$ | 3.0 | 1.7 | 4.4 | 3.8 | 3.4 | 5.9 | 5.8 | 6.9 | 8.4 |
| Trimethylpentanes | 81.8 | 90.6 | 76.2 | 79.6 | 86.2 | 79.1 | 80.4 | 81.1 | 78.0 |
| Other $C_8$'s | 7.6 | 4.4 | 11.8 | 8.0 | 4.8 | 8.5 | 6.7 | 6.8 | 6.7 |
| $C_9^+$ | 7.6 | 3.3 | 7.6 | 8.6 | 5.6 | 6.5 | 7.1 | 5.1 | 7.0 |
| $C_6^+$ MONC | 95.2 | 97.1 | 93.8 | 94.8 | 96.3 | 94.4 | 94.7 | 95.1 | 94.6 |

Runs 6 and 7 show that a rather small benefit in alkylate octane number is achieved when butene-1 is isomerized to butene-2 in the presence of a sulfuric acid catalyst relative to that shown in Runs 1 and 2 when using a fluorosulfuric acid catalyst, all runs being conducted at the same isobutene concentration. Similarly, Runs 4 and 5 show an enhancement that is absent in Runs 8 and 9. Thus, in contrast to the data in U.S. Pat. No. 2,591,367 shown above, the sulfuric acid catalyst is relatively insensitive to the composition of the olefin feedstock. Runs 3-5 emphasize further the trend shown by Runs 4 andd 5, i.e. that an alkylate of improved octane is obtained when using a fluorosulfuric acid catalyst as the amount of butene-1 in the feed decreases.

EXAMPLE 3

Fluorosulfuric Acid Alkylation of Pure Pentenes

The procedure of Example 1 was followed using the feedstocks and conditions shown below. The results obtained are shown in Table 3.

Table 3

| Olefin | Pentene-2 | Pentene-1 | 2-Methyl Butene-1 | 2-Methyl Butene-2 |
|---|---|---|---|---|
| Catalyst | | | | |
| Water/Acid, Mole Ratio | | 0.35 | | |
| Organic promoter, wt.% on total cat. | | 8 | | |
| Feed Composition, Vol. % | | | | |
| Olefin | 10.5 | 9.5 | 6.6 | 10.9 |
| Isobutane | 77.6 | 81.0 | 84.0 | 79.7 |
| n-paraffins | 11.9 | 9.5 | 9.4 | 9.5 |
| Operating Conditions | | | | |
| Temperature, °F | | 40 | | |
| Olefin Space Vel. v/h/v | 0.106 | 0.096 | 0.067 | 0.11 |
| Emulsion Circulation Rate, gpm | 24 | 24 | 25 | 25 |
| $C_6^+$ MONC | 88.0 | 90.3 | 92.9 | 93.1 |

This example shows that the branched pentene isomers produce better product quality alkylate than do the linear pentenes. It also shows that for linear pentenes, shifting the double bond to a more external position will produce an alkylate of improved quality.

What is claimed is:

1. In an alkylation process which comprises contacting a feed containing linear pentene-1 and linear pentene-2 with a paraffin at alkylation conditions in the presence of a catalyst comprising a strong acid selected from the group consisting of halosulfuric acid, trihalomethanesulfonic acid and mixtures thereof, the improvement which comprises (1) contacting said feed with an isomerization catalyst at isomerization conditions to convert at least a portion of said pentene-2 to pentene-1 prior to subjecting said feed to alkylation conditions and (2) recovering an alkylate of enhanced octane number relative to the alkylate obtained in the absence of the isomerization step (1).

2. The process of claim 1 wherein there is additionally added to the strong acid from about 5 to 100 mole %, based on acid, of (1) water, (2) a $C_1$-$C_7$ saturated aliphatic monohydroxy alcohol, or (3) a mixture of water and said alcohol.

3. The process of claim 1 wherein said alkylation is conducted at a temperature of from about −80° to 100° F, at a pressure of from about 1 to 20 atmospheres and at an olefin space velocity of from about 0.05 to 1000 volumes of olefin per hour per volume of catalyst.

4. The process of claim 1 wherein said catalyst is supported on a solid carrier.

5. The process of claim 1 wherein said alkylation is conducted substantially in the liquid phase.

6. The process of claim 1 wherein the paraffin is a $C_2$-$C_{10}$ paraffin.

7. The process of claim 6 wherein the $C_2$-$C_{10}$ paraffin is a $C_4$-$C_6$ isoparaffin.

8. The process of claim 6 wherein the catalyst comprises fluorosulfuric acid and about 5 to 100 mole % water, based on acid.

* * * * *